United States Patent [19]

Das

[11] Patent Number: 4,611,006

[45] Date of Patent: Sep. 9, 1986

[54] 5,6-EPOXY-7-OXABICYCLOHEPTANE SUBSTITUTED ETHERS USEFUL IN THE TREATMENT OF THROMBOTIC DISEASE

[75] Inventor: Jagabandhu Das, Plainsboro, N.J.

[73] Assignee: E. R. Squibb & Sons, Inc., Princeton, N.J.

[21] Appl. No.: 749,912

[22] Filed: Jun. 28, 1985

[51] Int. Cl.[4] .................. A61K 31/335; C07D 307/00; A61K 31/557

[52] U.S. Cl. ..................................... 514/468; 549/459

[58] Field of Search .......................... 549/459; 514/468

[56] References Cited

U.S. PATENT DOCUMENTS

| | | | |
|---|---|---|---|
| 4,073,933 | 2/1978 | Shimomura | 560/120 |
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

Primary Examiner—Henry R. Jiles
Assistant Examiner—Bernard I. Dentz

Attorney, Agent, or Firm—Lawrence S. Levinson; Burton Rodney

[57] ABSTRACT

5,6-Epoxy-7-oxabicycloheptane substituted ether prostaglandin analogs are provided having the structural formula

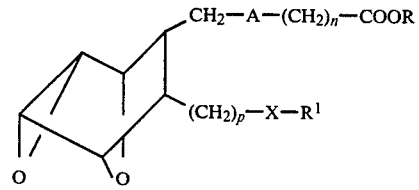

wherein X is O or

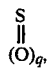

and including all stereoisomers thereof.

The compounds are cardiovascular agents useful, for example, in the treatment of thrombotic disease.

15 Claims, No Drawings

5,6-EPOXY-7-OXABICYCLOHEPTANE SUBSTITUTED ETHERS USEFUL IN THE TREATMENT OF THROMBOTIC DISEASE

DESCRIPTION OF THE INVENTION

The present invention relates to 5,6-epoxy-7-oxabicycloheptane substituted ether prostaglandin analogs which are cardiovascular agents useful, for example, in the treatment of thrombotic disease and are also useful as antiinflammatory agents. These compounds have the structural formula

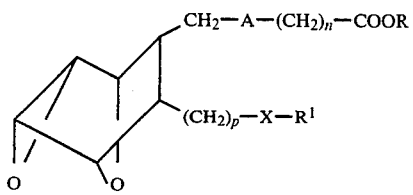

and including all stereoisomers thereof, wherein A is —CH=CH— or —(CH$_2$)$_2$, n is 0 to 8, p is 1 to 5, X is 0 or

wherein q is 0, 1 or 2; R is H, lower alkyl, alkali metal or polyhydroxylamine salt such as tris(hydroxymethyl)amino methane or glucamine, and R$^1$ is lower alkyl, aryl, aralkyl, cycloalkyl, cycloalkylalkyl, lower alkenyl or lower alkynyl. Thus, the compounds of the invention include the following types of compounds:

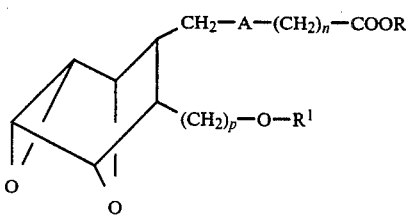

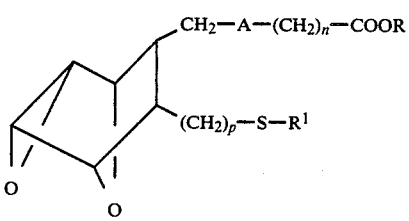

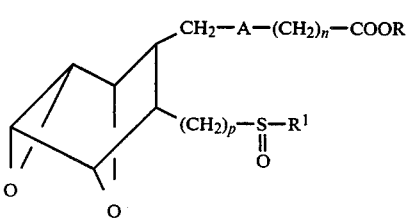

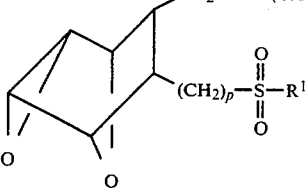

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, isobutyl, pentyl, hexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkylaryl substituent, a haloaryl substituent, a cycloalkyl substituent, an alkylcycloalkyl substituent, hydroxy, an alkylamino substituent, or an alkylthio substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups, an aryl group, 1 or 2 hydroxy groups, 1 or 2 alkylamino groups, or 1 or 2 alkylthio groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein substituent on either the phenyl or naphthyl may be 1 or 2 lower alkyl groups, 1 or 2 halogens (Cl, Br or F), 1 or 2 lower alkoxy groups, 1 or 2 hydroxy groups, 1 or 2 alkylamino groups, or 1 or 2 alkylthio groups.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The term "halogen" or "halo" as used herein by itself or as part of another group refers to chlorine, bromine, fluorine or iodine, with chlorine being preferred.

The terms "$(CH_2)_n$" and "$(CH_2)_p$" include a straight or branched chain radical having 1 to 8 carbons in the normal chain in the case of "$(CH_2)_n$" and 1 to 5 carbons in the normal chain in the case of "$(CH_2)_p$" and may contain one or more lower alkyl substituents. Examples of $(CH_2)_n$ and $(CH_2)_p$ groups include

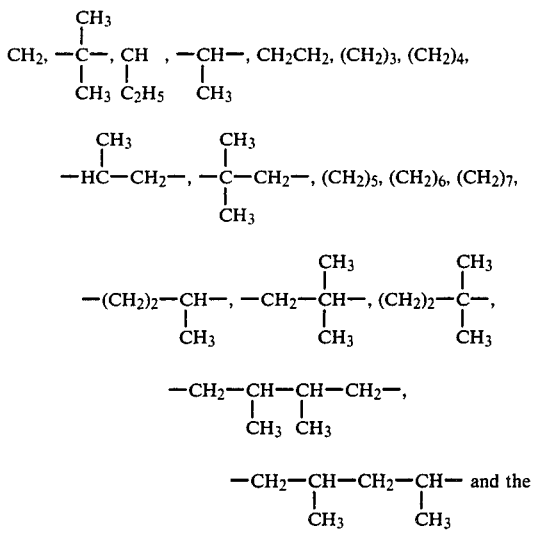

Preferred are those compounds of formula I wherein A is —CH=CH— or —$CH_2$—$CH_2$—, n is 3 to 5, p is 1, X is O or S, R is H, and $R^1$ is lower alkyl, such as propyl or hexyl, aryl, such as phenyl, or aralkyl such as benzyl.

The various compounds of the invention may be prepared as outlined below.

The 7-oxabicycloheptane ether compounds of formula I of the invention wherein X is O, p is 1, A is CH=CH or $CH_2$—$CH_2$, and n is 0 to 8, that is,

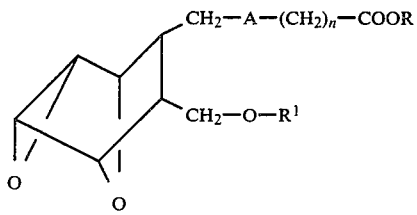   IE may be prepared starting with the alcohol II

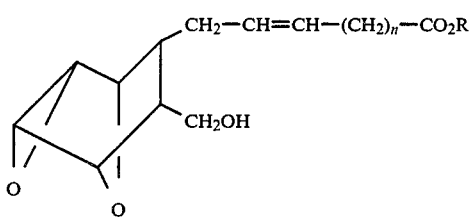   II (where R is lower alkyl)

which is subjected to an ether formation reaction wherein compound II is reacted with a strong base such as KOH, NaOH or LiOH and the like in the presence of an inert solvent, such as xylene, toluene, benzene or mesitylene and then after partial removal of solvent, reacting with a sulfonate compound of the structure

| | |
|---|---|
| Mesyl-$OR^1$ or | A |
| Tosyl-$OR^1$ | A' | or a halide of the structure

| | |
|---|---|
| $R^1$X (X is Cl or Br) | A'' | to form the ether

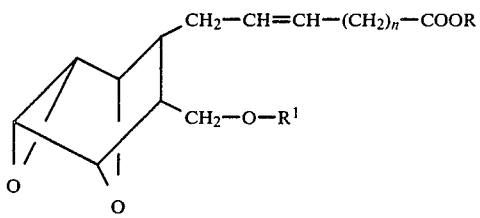   IF

Ether IF is then hydrolyzed by treating with strong base such as LiOH, KOH or NaOH to form the corresponding alkali metal salt and then neutralizing with a strong acid such as HCl or oxalic acid to form IG

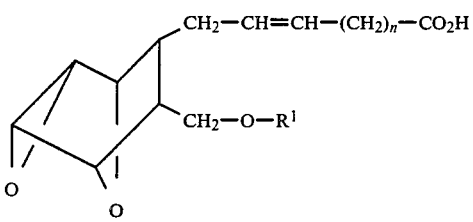   IG

Compounds of the invention wherein X is 0, A is $CH_2$—$CH_2$ and n is 0 to 8 may be prepared by subjecting acid IG to hydrogenation by treating IG with hydrogen in the presence of a catalyst such as palladium and inert solvent such as tetrahydrofuran to form acid IH

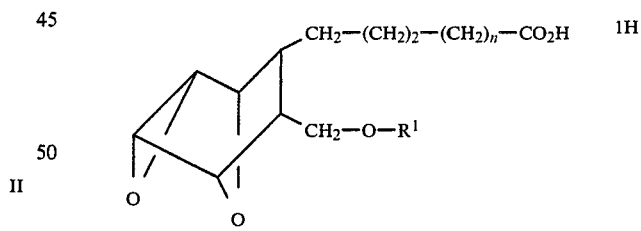   IH

Compounds of formula I wherein X is S, A is CH=CH, P is 1 may be prepared by starting with the hydroxymethyl compound II

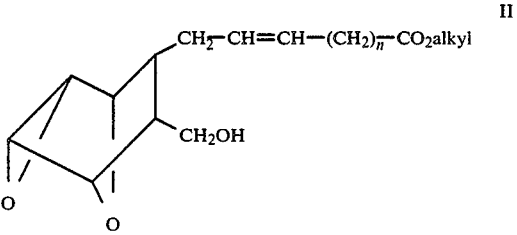   II and subjecting II to a tosylation reaction, for example, by reacting the hydroxymethyl compound with tosyl chloride in pyridine and methylene chloride to form the corresponding tosylate III

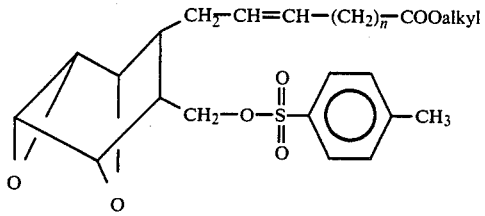

Thereafter, tosylate III is reacted with a thiol or mercaptan of the structure B $$HSR^1 \quad\quad B$$

in the presence of potassium t-butoxide and a solvent such as tetrahydrofuran, dimethyl sulfoxide or dimethylformamide to form compounds of the invention of the structure IV

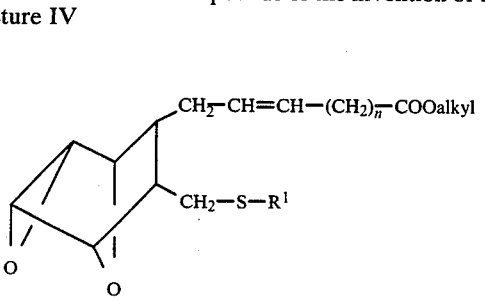

Ester IV may then be hydrolyzed by treating with strong alkali metal base and then neutralizing with a strong acid, as described hereinbefore, to form the acid

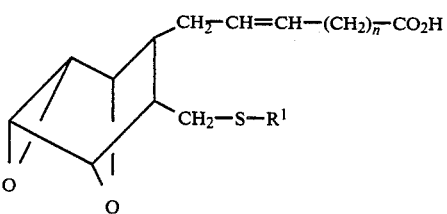

Compounds of the invention wherein p is 1, X is S, A is $CH_2$—$CH_2$ and n is 0 to 8 may be prepared by subjecting the hydroxymethyl compound II to hydrogenation by treating II with hydrogen in the presence of a catalyst such as palladium and an inert solvent such as tetrahydrofuran to form hydroxymethyl compound IIA

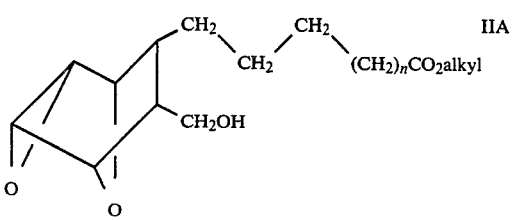

Compound IIA is then subjected to a tosylation reaction, for example, by reacting the hydroxymethyl compound with tosyl chloride in pyridine and methylene chloride to form the corresponding tosylate IIIA

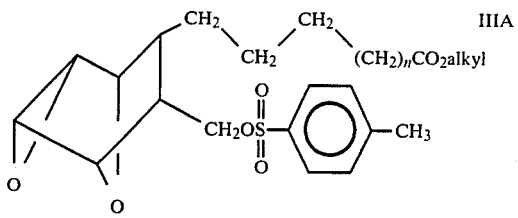

Thereafter, tosylate IIIA is reacted with a thiol or mercaptan of the structure B, above, in the presence of potassium t-butoxide and a solvent, such as tetrahydrofuran, dimethylsulfoxide, or dimethylformamide to form compounds of the invention of structure IK

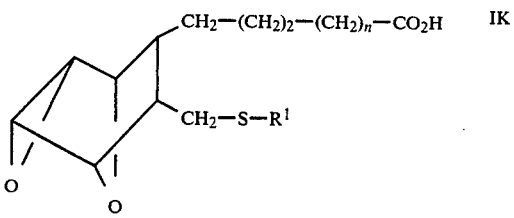

Compounds of formula I wherein p is 2 to 5 may be prepared by subjecting hydroxymethyl compound II wherein A is CH=CH or hydroxymethyl compound IIA wherein A is —$(CH_2)_2$—

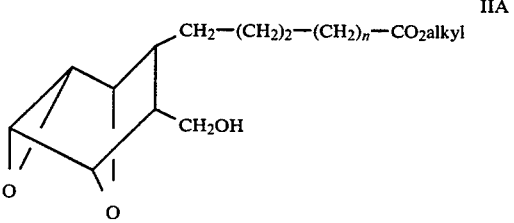

(formed by reducing II by treating with hydrogen in the presence of a palladium on carbon catalyst) to a Collins oxidation by reacting II or IIA with chromium trioxide in the presence of a basic solvent such as pyridine or dichloromethane to form aldehyde V. Aldehyde V

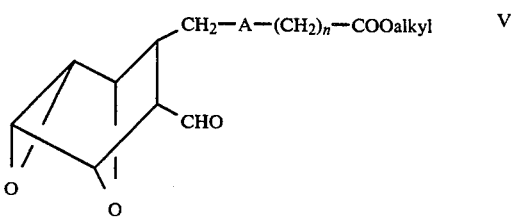

wherein A is CH=CH or $CH_2$—$CH_2$ is subjected to a homologation sequence, such as a Wittig reaction with $(C_6H_5)_3P^+Cl^-CH_2OCH_3$ followed by hydrolysis, (p−1) times, to form aldehyde VI

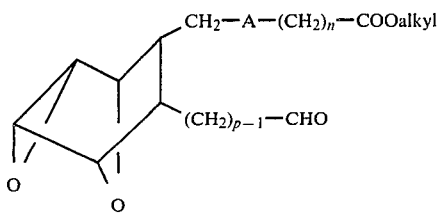   VI which is carried on to compounds of the invention where p is 2 to 5 by reducing aldehyde VI employing a reducing agent such as sodium borohydride in a solvent such as methanol to form alcohol ester VII To form compounds of formula I wherein X is

the sulfide derivative of formula I wherein X is S is subjected to an oxidation reaction, for example, by reacting same with sodium periodate, in the presence of methanol and tetrahydrofuran, to form the corresponding sulfinyl derivative

and sulfonyl derivative

The sulfinyl and sulfonyl derivatives may be separated by chromatography or other conventional separation procedures.

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The starting hydroxymethyl compound II may be prepared as follows. Dione, having the structure C

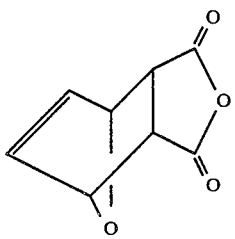   C that is, 7-oxabicyclo[2.2.1]-5-heptene-2,3-dicarboxylic anhydride [Ber.62, 554 (1929; Ann. 460, 98 (1928)] is reduced, for example, by reacting the dione with lithium aluminum hydride or diisobutyl aluminum hydride in the presence of an inert organic solvent such as tetrahydrofuran, ether or toluene at reduced temperatures of from about −78° C. to about 67° C. to form a diol D of the structure

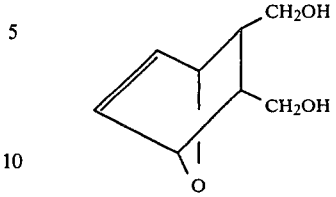   D

The diol D is subjected to a chloroformylation reaction by reacting D dissolved in an inert organic solvent as described above, with phosgene in the presence of a solvent such as tetrahydrofuran, toluene, benzene or xylene, to form an alcohol of the structure E

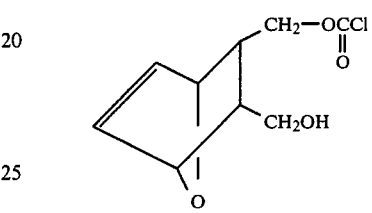   E

The alcohol E is dissolved in an inert organic solvent such as methylene chloride, tetrahydrofuran or ether and then reacted with an organic base, such as pyridine, triethylamine, N,N-dimethylaminopyridine or diazabicycloundecane (DBU) at reduced temperatures of from about −78° C. to about 25° C., to form cyclic carbonate F

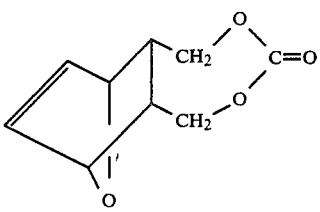   F

The cyclic carbonate F is then subjected to alcoholysis by reacting F with an alkanol (alkyl-OH) having from 1 to 12 carbons, such as ethanol, n-propanol, isopropanol, butanol, pentanol, hexanol, heptanol, octanol, nonenol or decanol, including all the various isomers thereof, preferably isopropyl alcohol, employing a molar ratio of D:alkanol of within the range of from about 1:10 to about 1:100 to form hydroxycarbonate G

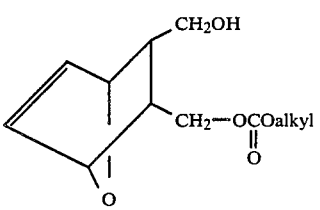   G (wherein alkyl contains 1 to 12 carbons as defined herein).

Thereafter, the hydroxy carbonate G is then tosylated (or otherwise protected) by reacting G (dissolved in methylene chloride, and a basic solvent such as pyridine, triethylamine or dimethylaminopyridine) with tosyl chloride or other protecting agent, such as methane sulfonyl chloride (mesyl chloride) and trifluoromethanesulfonic anhydride, to form the tosylate H or other protected compound

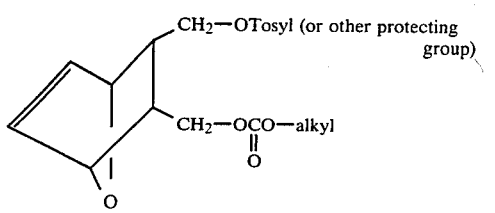

Then, the tosylate H dissolved in an inert solvent such as dimethylsulfoxide, or dimethylformamide is cyanated by reacting IV with an alkali metal cyanide such as NaCN or KCN employing a molar ratio of IV:cyanide of within the range of from about 1:1 to about 10:1, at elevated temperatures of from about 80° C. to about 130° C., in an inert atmosphere, such as an argon atmosphere, to form the cyanocarbonate J

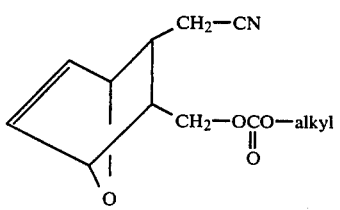

Cyanocarbonate J is dissolved in an alcohol such as methanol or ethanol and treated with aqueous alkali metal carboante such as potassium carbonate at reduced temperature to form the cyano alcohol K

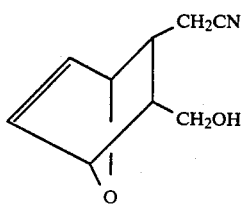

which is made to undergo tetrahydropyranyl ether formation by reacting cyano alcohol K with dihydropyran in the presence of an inert organic solvent such as methylene chloride or ether and catalytic amount of p-toluene sulfonic acid at reduced temperatures of from about 0° C. to about 10° C., to form the tetrahydropyranyl ether of formula L

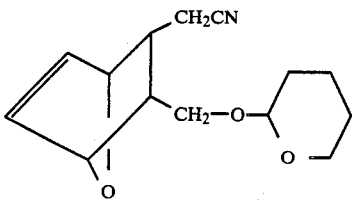

Compound L is then made to undergo epoxide formation by treating a solution of L in methylene chloride or other appropriate solvent with m-chloroperoxybenzoic acid at reduced temperatures to form epoxy nitrile M (which itself is a novel compound)

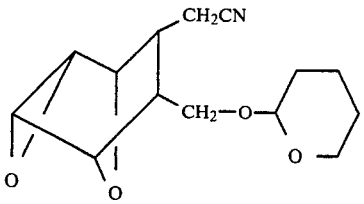

Compound M is then treated with diisobutyl aluminum hydride (DIBALH) in the presence of an inert solvent such as toluene or tetrahydrofuran at reduced temperatures of from about −70° to about −85° C. to form epoxy aldehyde N

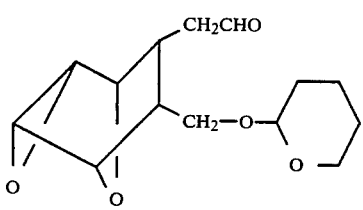

Epoxy aldehyde N in appropriate solvent such as tetrahydrofuran is then reacted with a suspension formed by mixing dry carboxylalkyltriphenylphosphonium halide O $$(C_6H_5)_3P^+ \cdot Br^- -(CH_2)_{n+1}COOH \qquad O$$

in tetrahydrofuran with potassium t-amylate in toluene at reduced temperature and the reaction product treated with etheral diazoalkane to form the ester P

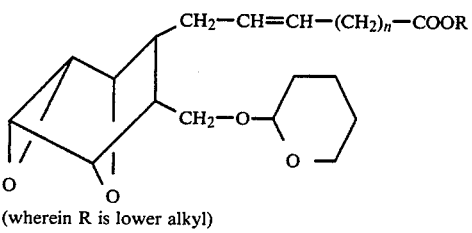

(wherein R is lower alkyl)

Compound P is dissolved in methanol and is then hydrolyzed by treatment with strong acid such as HCl, amberlyst resin or acetic acid to form alcohol II

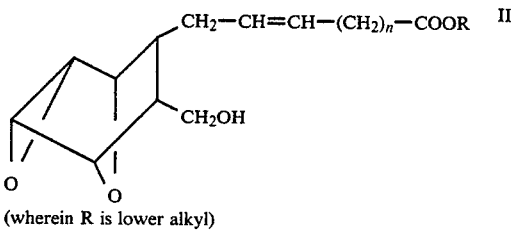

(wherein R is lower alkyl)

The compounds of this invention have four centers of asymmetry as indicated by the asterisks in formula I. However, it will be apparent that each of the formulae set out above which do not include asterisks still represent all of the possible stereoisomers thereof. All of the various steroisomeric forms are within the scope of the invention.

The varoius stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such steroisomers are set out below.

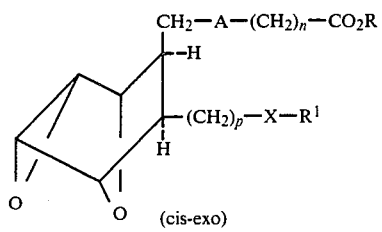 Ia
(cis-exo)

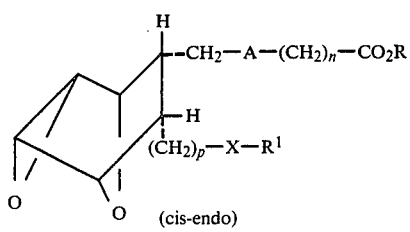 Ib
(cis-endo)

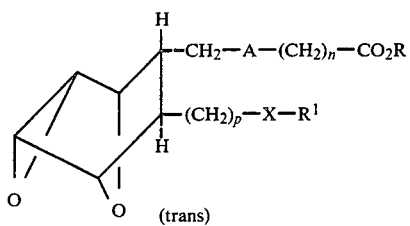 Ic
(trans)

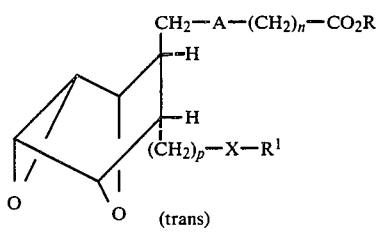 Id
(trans)

The nucleus in the compounds of the invention are depicted as

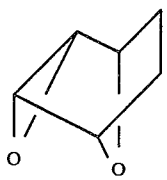

for matter of convenience; it will also be appreciated that the nucleus in the compounds of the invention may be depicted as

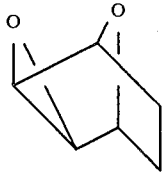

The compounds of this invention are cardiovascular agents useful as platelet aggregation inhibitors, such as inhibiting arachidonic acid-induced platelet aggregation (e.g., for treatment of thrombotic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris.

The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws "Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling, tenderness, pain and stiffness in conditions such as rheumatoid arthritis.

The compounds of this invention may also be used in combination with a cyclic AMP phosphodiesterase (PDE) inhibitor such as theophylline or papaverine in the preparation and storage of platelet concentrates.

The compounds of the invention can be administered orally or to various mammalian species known to to such maladies, e.g., humans, cats, dogs, and the like in an effective amount within the dosage range of about 1 to 100 mg/kg, preferab 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of the invention. Unless otherwise indicated, all temperatures are expressed in degrees Centigrade.

EXAMPLE 1

[1α,2β(5Z),3β,4α,5α,6α]-7-[5,6-Epoxy-3-[(hexylthio)-methyl]-7-oxabicyclo[2.2.1]hept-1-yl]-5-heptenoic acid, methyl ester

A. 7-Oxabicyclo[2.2.1]-5-heptene-2,3-dimethanol

To a suspension of 6.84 g of lithium aluminum hydride (180 mmole) in 200 ml of freshly distilled THF, cooled in an ice-water bath was added dropwise, a solution of 20 g 7-oxabicyclo-[2.2.1]-5-heptene-2,3-dicarboxylic anhydride (120 mmole) in 150 ml of dry THF, over a period of one hour. After the addition, the cooling bath was removed and the reaction mixture was stirred at room temperature for 24 hours. The reaction mixture was now cooled in ice-water bath and excess of hydride was destroyed by slow addition of freshly prepared saturated sodium sulfate solution. Addition was continued until all the inorganic salts were precipitated as white granular solids. Anhydrous magnesium sulfate was added to the reaction mixture and it was filtered. The residue was thoroughly washed with methylene chloride. The residue was taken up in 500 ml of 10% acetonitrile in ethyl acetate, stirred for 30 minutes and finally was filtered. The combined filtrate was concentrated under reduced pressure. The crude residue was chromatographed on a silica gel column. Elution with 50% ethyl acetate in hexane, followed by ethyl acetate and finally with 10% methanol in ethyl acetate afforded 17.25 g of diol as a colorless viscous oil.

B. 7-Oxabicyclo[2.2.1]-5-heptene-2,3-dimethanol carbonate

To a solution of 16.73 g of Part A diol (107.4 mmole) in 200 ml of freshly distilled THF, cooled in an ice-water bath was added dropwise 90 ml of a 12.5% by weight solution of phosgene in toluene (112.5 mmole), over a period of 45 minutes. The reaction mixture was stirred for additional 15 minutes, whereupon argon was bubbled through to remove excess of phosgene and hydrogen chloride formed during the reaction. The reaction mixture was now concentrated under reduced pressure. The crude monochloroformate was now dissolved in 250 ml of methylene chloride and cooled at −50° C. in a dry ice-acetone bath. A solution of 25 ml of pyridine in 50 ml of methylene chloride was now added dropwise over a period of 20 minutes. An immediate white precipitate was formed upon addition. The reaction mixture was left at −50° C. for an additional 30 minutes, whereupon the cooling bath was removed and the reaction mixture was washed thoroughly with water. The methylene chloride layer was dried over anhydrous magnesium sulfate, filtered and the filtrate was concentrated under reduced pressure. The crude residue was triturated with ether, cooled at 0° C. and the precipitated title carbonate was filtered off. 15.25 g of white crystalline title carbonate was obtained.

C. 2-Hydroxymethyl-3-isopropyloxycarbonyloxymethyl-7-oxabicyclo[2.2.1]heptene To a suspension of 15.25 g of Part B cyclic carbonate (83.8 mmole) in 200 ml of isopropyl alcohol was added with stirring 1 g of p-toluene sulfonic acid. The reaction mixture was heated under reflux for 8 hours whereupon it was cooled and isopropanol was removed by distillation under reduced pressure. The crude residue was dissolved in methylene chloride and washed with aqueous sodium bicarbonate solution. The aqueous layer was extracted several times with methylene chloride. The combined methylene chloride extract was dried over anhydrous magnesium sulfate and was then concentrated under reduced pressure to obtain 22.53 g of title isopropyloxycarbonate as a viscous oil.

D. 2-p-Toluenesulfonyloxymethyl-3-isopropyloxycarbonyloxymethyl-7-oxabicyclo[2.2.1]heptene To a solution of 22.53 g of Part C isopropyloxycarbonate (84 mmole) in 100 ml of pyridine was added with stirring 19.2 g of p-toluene sulfonyl chloride (101 mmole) at 0°-5° C. The reaction mixture was stirred at room temperature for 24 hours, whereupon it was diluted with methylene chloride and washed thoroughly with water, saturated copper sulfate solution and finally with water. The combined aqueousl layer was extracted with two 200 ml portions of methylene chloride. The combined methylene chloride extract was dried over anhydrous magnesium sulfate and finally was concentrated under reduced pressure. The crude residue was triturated with ether, cooled at 0° C. and the precipitate title tosylate (28.3 g) was filtered off. The mother liquor was concentrated and chromatographed on a silica gel column to obtain additional 5.2 g of crystalline title tosylate (eluting solvent 15-30% ethyl acetate in hexane).

E. 2-Cyanomethyl-3-isopropyloxycarbonyloxymethyl-7-oxabicyclo[2.2.1]heptene

To a solution of 5.3 g of Part D tosylate (12.99 mmole) in 50 ml of dry dimethylsulfoxide was added with stirring 1.28 g of powdered sodium cyanide (26 mmole). The reaction mixture was placed on an oil-bath (bath temperature 90°-95° C.) and heated for 2 hours. It was now cooled and diluted with 200 ml of ether. The reaction mixture was now thoroughly washed with water. The combined aqueous extract was extracted with two 150 ml of ether. The ether layer was now dried over anhydrous magnesium sulfate and concentrated under reduced pressure. The crude residue was chromatographed on a silica gel column. Elution with 25-50% ethyl acetate in hexane afforded 2.58 g of title cyano-carbonate.

F. 2-Cyanomethyl-3-hydroxymethyl-2-oxabicyclo[2.2.1]heptene

To a solution of 1 g of potassium carbonate in 25 ml of water and 75 ml of methanol, cooled in an ice-water bath was added with stirring a solution of 2.58 g of Part E cyano-carbonate (9.8 mmole) in 10 ml of methanol. After 15 minutes, the cooling bath was removed and the reaction mixture was allowed to stand at room temperature for additional 6 hours, whereupon it was acidified with 1 N aqueous hydrochloric acid solution. Most of methanol was now removed by distillation under reduced pressure. The residue was now exhaustively extracted with methylene chloride (X12) (after saturating it with sodium chloride). The combined organic extract was dried over anhydrous magnesium sulfate and concentrated under reduced pressure. The crude residue was chromatographed on a silica gel column and eluted with 25-50% ethyl acetate in hexane, followed by ethyl acetate to obtain 1.23 g of cyano-alcohol.

G.
2-Cyanomethyl-3-tetrahydropyranyloxymethyl-7-oxabicyclo[2.2.1]heptene A solution of 1.23 g of Part F cyano-alcohol (7.36 mmole) in 20 ml of dry methylene chloride was treated with 800 ml of dihydropyran (8.89 mmole) and catalytic amount of p-toluene sulfonic acid at 0°–5° C. After 4 hours, the reaction mixture was diluted with ether and washed with aqueous sodium bicarbonate solution. The aqueous layer was reextracted twice with ether. The combined organic extract was dried over anhydrous magnesium sulfate and concentrated under reduced pressure. The crude residue was chromatographed on a silica gel column and eluted with 20–25% ethyl acetate in hexane to obtain 1.61 g of title tetrahydropyranyl ether.

H.
5,6-Epoxy-2-cyanomethyl-3-tetrahydropropyloxymethyl-7-oxabicyclo[2.2.1]heptene A solution of 1.61 g of Part G cyano ether (6.4 mmole) in 20 ml of dry methylene chloride was treated with 1.66 g of 80% pure m-chloroperoxybenzoic acid (9.6 mmole) at 0°–5° C. After a few minutes, the cooling bath was removed and the reaction mixture was let stand at room temperature for 6 hours. The reaction mixture was now diluted with ether and excess of peracid was decomposed by addition of aqueous sodium meta-bisulfite solution. After stirring for 30 minutes, the organic layer was separated and the aqueous layer was extracted twice with methylene chloride. The combined organic extract was dried over anhydrous magnesium sulfate and concentrated under reduced pressure. Purification by chromatography on a silica gel column (eluting solvent 25–67% ethyl acetate in hexane) afforded 1.58 g of title epoxide.

I.
5,6-Epoxy-2-formylmethyl-3-tetrahydropyranyloxymethyl-7-oxabicyclo[2.2.1]heptene heptene 5.88 mmole) in 25 ml of toluene, cooled at −78° C. in a dry ice-acetone bath was added with stirring, 6.8 ml of a 25% by weight solution of diisobutylaluminumhydride in toluene (∼12 mmole), dropwise over a period of 5 minutes. After 4 hours at −78° C., excess of hydride was destroyed by dropwise addition of 1 ml of glacial acetic acid. The cooling bath was removed and 20 g of silica gel was added to the reaction mixture with stirring, followed by 1.5 ml of water dropwise. Stirring was continued for 30 minutes, whereupon the reaction mixture was filtered and the residual silica gel was washed successively with THF, 5% acetonitrile in ethyl acetate and finally with acetone. The combined filtrate was concentrated under reduced pressure and the crude residue was chromatographed on a silica gel column. Elution with 50% ethyl acetate in hexane, followed by ethyl acetate afforded 1.16 g of title epoxyaldehyde, which crystallized on standing at −20° C.

J.
[1α,2β(5Z),3β,4α,5α,6α]-7-[5,6-Epoxy-3-(tetrahydropyranyloxymethyl)-7-oxabicyclo[2.2.1]hept-2-yl]-5-heptenoic acid, methyl ester A suspension of 5.77 g of freshly dried carboxybutyltriphenylphosphonium bromide (13.03 mmole), in 50 ml of freshly distilled THF, cooled in an ice-water bath was treated dropwise with 12 ml of a 1.5 M solution of K-t-amylate in toluene (19.2 mmole). The yellow-orange suspension was stirred at 0° C. for 30 minutes and finally at room temperature for 1 hour, whereupon it was cooled to −20° C. and a solution of 2.33 g of Part I epoxy aldehyde (8.69 mmole) in 10 ml of dry THF was added dropwise over a period of several minutes. An instant discolorization of the yield solution was observed. The reaction mixture was stirred at −20° C. for 2 hours, whereupon it was warmed to 0° C. and left for 15 minutes, prior to addition of glacial acetic acid. The reaction mixture was now diluted with ether and washed with water. The ether extract was washed several times with saturated sodium bicarbonate solution. The combined aqueous extract was now washed with ether (X2). The aqueous layer was now carefully acidified with 1 N aqueous hydrochloric acid to pH 2. It was now extracted with ether and then with methylene chloride. The combined ether and methylene chloride extract were dried over anhydrous magnesium sulfate and concentrated under reduced pressure. The crude residue was diluted with 75 ml of ether, cooled in an ice-water bath and an etheral diazomethane solution was added dropwise until the color persisted. After 30 minutes, excess diazomethane was removed by bubbling argon through the reaction mixture. It was now concentrated and the crude residue was chromatographed on a silica gel column. Elution with 15–40% ethyl acetate in hexane afforded 1.27 g of title 5Z-ester (contaminated with 10–15% of undesired 5E ester).

K.
[1α,2β(5Z),3β,4α,5α,6α]-7-[5,6-Epoxy-3-hydroxymethyl-7-oxabicyclo[2.2.1]hept-2-yl]-5-heptenoic acid, methyl ester To a solution of 1.27 g of Part J tetrahydropyranyl ether (3.46 mmole) in 30 ml of methanol was added with stirring 250 mg of powdered and dried Amberlyst-15. After 6 hours at room temperature, the reaction mixture was diluted with ether and anhydrous magnesium sulfate was added. It was now filtered and the residual solid was washed thoroughly with ether. The combined organic extract was dried over anhydrous magnesium sulfate and concentrated under reduced pressure. The crude residue was chromatographed on a silica gel column and eluted with 50–75% ethyl acetate in hexane to obtain 892 mg of title alcohol ester.

L.
[1α,2β(5Z),3β,4α,5α,6α]-7-[5,6-Epoxy-3-[(tosyloxy)-methyl]-7-oxabicyclo[2.2.1]hept-2-yl]-5-heptenoic acid, methyl ester To 116 mg of Part K alcohol (0.41 mmole) in 2 ml of pyridine at 25° C. was added 156 mg of toluenesulfonyl chloride (0.82 mmole, 2 equiv.). After stirring at 25° C. for 5 hours, the mixture was diluted with 40 ml of ether and washed with three 10 ml portions of a saturated copper sulfate solution, and two 10 ml portions of $H_2O$. The organic layer was dried over anhydrous $MgSO_4$ and concentrated to give 190 mg of a crude oil which consisted of title tosylate and some tosyl chloride.

M.
[1α,2β(5Z),3β,4α,5α,6α]-7-[5,6-Epoxy-3-[(hexylthio)-methyl-7-oxabicyclo[2.2.1]hept-2-yl]-5-heptenoic acid, methyl ester To a slurry of 200 mg of potassium tert.butoxide (1.78 mmole, 3.9 equiv.) in 6 ml of dry tetrahydrofuran at 25° C. was added 542 mg of 1-hexanethiol (4.6 mmole, 10 equiv.). After stirring at 25° C. for 30 minutes, a solution of 222 mg of crude Part L tosylate (ca. 0.46 mmole) in 4 ml of dry THF was added and the mixture was heated at reflux for 30 minutes. The mixture was then cooled to 25° C. and diluted with 50 ml of ether. The ethereal solution was washed with two 10 ml portions of saturated NaHCO$_3$ solution and 10 ml of H$_2$O. The organic layer was dried over anhydrous MgSO$_4$ and concentrated. The residue was purified on a silica gel column, with 20% EtOAc/hexanes as eluting solvents, to give 124 mg of title ester as an oil.

EXAMPLE 2

[1α,2β(5Z),3β,4α,5α,6α]-7-[5,6-Epoxy-3-[(hexylthio)-methyl]-7-oxabicyclo[2.2.1]hept-2-yl]-5-heptenoic acid To a solution of 124 mg of Example 1 ester (0.32 mmole) in 4.5 ml of dry THF, saturated with argon, at 25° C. was added 1.5 ml of a 1 N lithium hydroxide solution (1.5 mmole, 5 equiv.). After stirring at 25° C. for 20 hours, the reaction mixture was concentrated. The residue was diluted with 5 ml of H$_2$O and acidified to pH 3 with a saturated oxalic acid solution. The aqueous solution was extracted with three 20 ml portions of ether. The combined organic layer was washed with two 10 ml portions of H$_2$O and dried over anhydrous MgSO$_4$ and concentrated to give 120 mg of a crude oily solid. This was recrystallized with methanol/ether to yield 77 mg of title product as a white solid.

TLC: silica gel; EtOAc/hexanes (2:1); R$_f$~0.4.

Analysis: Calc'd. for C$_{20}$H$_{32}$O$_4$S C, 65.18; H, 8.75; S, 8.70.

Found: C, 65.31; H, 8.72; S, 8.52.

EXAMPLE 3

[1α,2β(5Z),3β,4α,5α,6α]-7-[5,6-Epoxy-3-[(hexyloxy)-methyl]-7-oxabicyclo[2.2.1]hept-2-yl]-5-heptenoic acid A mixture of 40 mg of powdered KOH (0.71 mmole, 5 equiv.) in 10 ml of dry xylene was distilled off until ca. 5 ml of solution remained. To the cooled, remaining solution was added a solution of 40 ml of Example 1 Part K alcohol (0.14 mmole) and 122 mg of hexyl mesylate (0.71 mmole, 5 equiv.) in 5 ml of dry xylene. The resulting mixture was heated at reflux for 10 minutes, then cooled to 25° C. and diluted with 50 ml of ether. The ethereal solution was washed with two 10 ml portions of 1 N hydrochloric acid and 10 ml of H$_2$O. The aqueous layer was reextracted with 10 ml of ether. The combined organic layer was dried over anhydrous MgSO$_4$ and concentrated to yield 40 mg of a crude oil.

A second batch was run, under the same conditions as above, starting with 60 mg (0.21 mmole) of Example 1 Part K alcohol to give 70 mg of a crude product.

The crude products from the two above batches were combined and purified on a silica gel column, with 50% EtOAc/hexanes as eluting solvents, to give 72.8 mg of title product as an oil.

TLC: silica gel; EtOAc; R$_f$~0.65.

Analysis Calc'd for C$_{20}$H$_{35}$O$_5$ C, 68.15; H, 9.15.

Found: C, 68.36; H, 8.94.

EXAMPLE 4

[1β,2α(Z),3α,4β,5α,6α]-7-[5,6-Epoxy-3-[(propylthio)-methyl]-7-oxabicyclo-[2.2.1]hept-2-yl]-5-heptenoic acid, methyl ester To a slurry of 81 mg of potassium-tertbutoxide (0.72 mmole, 4.2 equiv.) in 2 ml of dry tetrahydrofuran at 25° C. was added 129 mg of 1-propanethiol (1.7 mmole, 10 equiv.). After stirring at 25° C. for 30 minutes, a solution of 60 mg of Example 1 Part L was heated at reflux for 30 minutes. The mixture was then cooled to 25° C. and diluted with 20 ml of ether. The ethereal solution was washed with two 5 ml portions of saturated NaHCO$_3$ solution, 5 ml of H$_2$O. The organic layer was dried over anhydrous MgSO$_4$ and concentrated. The residue was purified on a silica gel column, with 20% EtOAc/hexanes as eluting solvents, to give 60 mg of title ester as an oil.

EXAMPLE 5

[1β,2α(Z),3α,4β,5α,6α]-7[5,6-Epoxy-3-[(propylthio)-methyl]-7-oxabicyclo[2.2.1]hept-2-yl]-5-heptenoic acid To a solution of 60 mg of Example 4 ester (0.17 mmole) in 1.7 ml of dry THF, saturated with argon, at 25° C. was added 1.7 ml of a 1 N lithium hydroxide solution (1.7 mmole, 10 equiv.). After stirring at 25° C. for 20 hours, the reaction mixture was concentrated. The residue was diluted with 3 ml of H$_2$O and acidified to pH 3 with a saturated oxalic acid solution. The aqueous solution was extracted with three 10 ml portions of ether. The combined organic layer was washed with two 50 ml portions of H$_2$O, then dried over anhydrous MgSO$_4$ and concentrated to give 54 mg of a crude oily solid. This was recrystallized with methanol/ether to give 38.2 mg of title product as a white solid.

TLC: silica gel; 5% MeOH/CH$_2$Cl$_2$; R$_f$~0.5.

Analysis: Calc'd for C$_{17}$H$_{26}$O$_4$S: C, 62.55; H, 8.03; S, 9.82.

Found: C, 62.46; H, 8.12; S, 9.58.

EXAMPLE 6

(1α,2β,3β,4α,5α,6α)-7-[5,6-Epoxy-3-[(hexyloxy)methyl]-7-oxabicyclo[2.2.1]hept-2-yl]heptanoic acid Example 3 compound (192 mg, 0.54 mmol) is dissolved in 5 ml ethyl acetate with several drops of acetic acid and hydrogenated with palladium on charcoal to form the title compound.

EXAMPLE 7

[1α,2β(5Z),3β,4α,5α,6α]-7-[5,6-Epoxy-3-(methyloxy)-methyl]-7-oxabicyclo[2.2.1]hept-2-yl]-5-heptenoic acid Following the procedure of Example 3 except substituting methyl methanesulfonate for n-hexyl methanesulfonate, the title compound is obtained.

EXAMPLE 8

(1α,2β,3β,4α,5α,6α)-7-[5,6-Epoxy-3-(butyloxy)methyl]-7-oxabicyclo[2.2.1]hept-2-yl]-5-heptenoic acid Following the procedure of Example 3 except substituting n-butyl methanesulfonate for n-hexyl methanesulfonate, the title compound is obtained.

EXAMPLE 9

[1α,2β(5Z),3β,4α,5α,6α]-7-[5,6-Epoxy-3-[(octyloxy)-methyl]-7-oxabicyclo[2.2.1]hept-2-yl-5-heptenoic acid Following the procedure of Example 3 except sustituting n-octyl methanesulfonate for n-hexyl methanesulfonate, the title compound is obtained.

EXAMPLE 10

[1α,2β(5Z),3β,4α,5α,6α]-7-[5,6-Epoxy-3-[(phenyloxy)-methyl]-7-oxabicyclo[2.2.1]hept-2-yl-5-heptenoic acid (a) Phenol (1 mmol) is added to a solution of triphenylphosphine (1 mmol), diethylazodicarboxylate (1 mmol) and title K alcohol from Example 1 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1α,2β(5Z),3β,4α,5α,6α]-7-[5,6-epoxy-3-[(phenyloxy)-methyl]-7-oxabicyclo[2.2.1]hept-2-yl]-5-heptenoic acid, methyl ester.

(b) Following the procedure as set out in Example 2, the ester from part (a) is converted to the title compound.

EXAMPLE 11

[1α,2β(5Z),3β,4α,5α,6α]-7-[5,6-Epoxy-3-[(ethyloxy)-methyl]-7-oxabicyclo[2.2.1]hept-2-yl]-5-heptenoic acid Following the procedure of Example 3 except substituting ethyl methanesulfonate for n-hexylmethane sulfonate, the title compound is obtained.

EXAMPLE 12

[1α,2β(5Z),3β,4α,5α,6α]-7-[5,6-Epoxy-3-[(benzyloxy)-methyl]-7-oxabicyclo[2.2.1]hept-2-yl]-5-heptenoic acid Following the procedure of Example 3 except substituting benzyl methanesulfonate for n-hexylmethanesulfonate, the title compound is obtained.

EXAMPLE 13

(1α,2β,3β,4α,5α,6α)-7-[5,6-Epoxy-3-[(benzyloxy)methyl]-7-oxabicyclo[2.2.1]hept-2-yl]heptanoic acid Following the procedure of Example 6 except substituting the Example 12 acid for the Example 3 acid, the title compound is obtained.

EXAMPLE 14

[1α,2β(5Z),3β,4α,5α,6α]-7-[5,6-Epoxy-3-[(cyclohexyloxy)methyl]-7-oxabicyclo[2.2.1]hept-2-yl]-5heptenoic acid Following the procedure of Example 3 except substituting cyclohexyl methanesulfonate for n-hexyl methanesulfonate, the title compound is obtained.

EXAMPLE 15

[1α,2β(5Z),3β,4α,5α6α]-7-[5,6-Epoxy-3-[(cyclopentyloxy)methyl]-7-oxabicyclo[2.2.1]hept-2-yl]-5-heptenoic acid Following the procedure of Example 3 except substituting cyclopentyl methanesulfonate for n-hexyl methanesulfonate, the title compound is obtained.

EXAMPLE 16

(1α,2β,3β,4α,5α,6α)-7-[5,6-Epoxy-3-[(cyclohexyloxy)-methyl]-7-oxabicyclo[2.2.1]hept-2-yl]heptanoic acid Following the procedure of Example 6 except substituting the Example 14 acid for the Example 3 acid, the title compound is obtained.

EXAMPLE 17

[1α,2β(5Z),3β,4α,5α,6α]-7-[5,6-Epoxy-3-[2-(hexyloxy)ethyl]-7-oxabicyclo[2.2.1]hept-2-yl]-5-heptenoic acid

A.

[1α,2β(5Z),3β,4α,5α,6α]-7-[5,6-Epoxy-3-formyl-7-oxabicyclo[2.2.1]-hept-2-yl]-5-heptenoic acid, methyl ester To a suspenion of 325 mg of pyridinium chlorochromate and 325 mg of celite in 20 ml of dry methylene chloride was added with stirring a solution of 211 mg of Example 1 Part K alcohol ester (0.75 mmole) in 2 ml of methylene chloride. After 4 hours at room temperature, the reaction mixture was diluted with 100 ml of ether and filtered through a pad of florisil. The florisil was washed several times with ether and ethyl acetate. The combined organic extract was washed with water, dried over anhydrous magnesium sulfate and was then concentrated under reduced pressure to obtain 174 mg of title aldehyde.

B.

[1α,2β(5Z),3β,4α,5α,6α]-7-[5,6-Epoxy-3-(2-oxo)ethyl]-7-oxabicyclo[2.2.1]-hept-2-yl]-5-heptenoic acid Into a dry 100 ml round bottom 3-necked flask containing a stir bar is added dried 12.9 g (37.7 mmoles) methoxymethyltriphenylphosphonium chloride (($C_6H_5$)$_3$P$^+$—$CH_2OCH_3Cl^-$) and 235 ml distilled toluene (stored over molecular sieves). The resulting suspension is stirred in an ice-bath, under argon, until cold and then a 1.55 M solution of 18.3 ml (28.3 mmol) of potassium t-amylate in toluene was added dropwise. A bright red solution formed which is stirred at 0° C. for an additional 35 minutes. Thereafter, a solution of (18.8 mmol) Part A aldehyde in 60 ml toluene is added by means of a dropping funnel over a 35 minutes period with the ice-bath still in place. The reaction is then quenched by addition of 2.3 g (39 mmol) acetic acid in 5 ml ether. The reaction mixture is immediately poured into 200 ml saturated NH$_4$Cl, and extracted with ether (4×200 ml). The combined ether phases are washed with NaCl saturated solution, and dried (MgSO$_4$) and concentrated to yield a yellow oil in a white crystalline solid (phosphine oxide). The white solid is triturated with EtOAc and the mother liquor is purified by chromatography on an LPS-1 silica column to obtain the title compound.

C.

[1α,2β(5Z),3β,4α,5α,6α]-7-[5,6-Epoxy-3-(2-hydroxyethyl)-7-oxabicyclo[2.2.1]-hept-2-yl]-5-heptenoic acid, methyl ester The aldehyde (1.47 g, 5 mmol) from part B in methanol (50 ml) is treated with NaBH$_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title C compound.

D.

[1β,2α(Z),3α,4β]-7-[3-(2-Hexyloxy)ethyl]-7-oxabicyclo[2.2.1]hept-2-yl]-5-heptenoic acid Following the procedure of Example 3 except substituting the above part C alcohol for the alcohol used in Example 3, the title compound is obtained.

EXAMPLE 18

[1α,2β(5Z),3β,4α,5α,6α]-7-[5,6-Epoxy-3-[2-(Benzyloxy)ethyl]-7-oxabcicylo[2.2.1]hept-2-yl]-5-heptenoic acid Following the procedure of Example 17 except substituting benzyl methanesulfonate for n-hexyl methanesulfonate, the title compound is obtained.

EXAMPLE 19

[1α,2β(5Z),3β,4α,5α,6α,]-7-[5,6-Epoxy-3-[2-(cyclopentyloxy)ethyl]-7-oxabicyclo[2.2.1]hept-2-yl]-5-heptenoic acid Following the procedure of Example 17 except substituting cyclopentyl methanesulfonate for n-hexyl methanesulfonate, the title compound is obtained.

EXAMPLE 20

[1α,2β(5Z),3β,4α,5α,6α]-7-[5,6-Epoxy-3-[2-(cyclohexyloxy)ethyl]-7-oxabicyclo[2.2.1]hept-2-yl]-5-heptenoic acid Following the procedure of Example 17 except substituting cyclohexyl methanesulfonate for n-hexyl methanesulfonate, the title compound is obtained.

EXAMPLE 21

1α,2β(5Z),3β,4α,5α,6α]-7-[5,6-Epoxy-3-[4-(hexyloxy)butyl]-7-oxabicyclo[2.2.1]hept-2-yl]-5-heptenoic acid

A.

[1α,2β(5Z),3β,4α,4α,5α,6α]-7-[5,6-Epoxy-[3-(3-oxo)-propyl]-7-oxabicyclo[2.2.1]-hept-2-yl]-5-heptenoic acid, methyl ester Following the procedure of Example 17, part B except substituting [1α,2β(5Z),3β,4α,5α,6α]-7-5,6-epoxy-[3-(2-oxo)ethyl]-7-oxabicyclo[2.2.1]hept-2-yl]-5-heptenoic acid, methyl ester for [1α,2β(5Z),3β,4α,5α,6α]-7-[5,6-epoxy-[3-formyl]-7-oxabicyclo[2.2.1]hept-2-yl]-5-heptenoic acid, methyl ester, the title A compound is obtained.

B.

[1α,2β(5Z),3β,4α,5α,6α]-7-[5,6-Epoxy-3-(4-oxo)butyl-7-oxabicyclo[2.2.1]hept-2-yl]-5-heptenoic acid, methyl ester Following the procedure of Example 17, part B, except substituting the aldehyde from part A above for [1α,2β(5Z),3β,4α,5α,6α]-7-[5,6-epoxy-[3formyl]-7-oxabicyclo[2.2.1]hept-2-yl]-5-heptenoic acid, methyl ester, the title B compound is obtained.

C.

[1α,2β(5Z),3β,4α,5α,6α]-7-[5,6-Epoxy-3-(4-hydroxybutyl)-7-oxabicyclo-[2.2.1]hept-2-yl]-5-heptenoic acid, methyl ester Following the procedure of Example 17, part C, except substituting the title B aldehyde for [1α,2β(5Z),3β,4α,5α,6α]-7-[5,6-epoxy-3-(2-oxyethyl)-7-oxabicyclo[2.2.1]hept-2-yl]-5-heptenoic acid, methyl ester, the title C alcohol is obtained.

D.

[1α,2β(5Z),3β,4α,5α,6α]-7-[5,6-Epoxy-3-[4-(hexyloxy)butyl]-7-oxabicyclo[2.2.1]-hept-2-yl]-5-heptenoic acid Following the procedure of Example 3, except substituting the above part C alcohol for the alcohol used in Example 3, the title compound is obtained.

EXAMPLE 22

[1α,2β(5Z),3β,4α,5α,6α]-7-[5,6-Epoxy-3-[4-(cyclohexyloxy)butyl]-7-oxabicyclo[2.2.1]hept-2-yl]-5-heptenoic acid Following the procedure of Example 21 except substituting cyclohexyl methanesulfonate for n-hexyl methanesulfonate, the title compound is obtained.

EXAMPLE 23

[1α,2β(5Z),3β,4α,5α,6α]-7-[5,6-Epoxy-3-[4-(phenyloxy)butyl]-7-oxabicyclo[2.2.1]hept-2-yl]-5-heptenoic acid Following the procedure of Examples 10 and 21 except substituting [1α,2β(5Z),3β,4α,5α,6α]-7-5,6-epoxy-3-(4-hydroxybutyl)-7-oxabicyclo[2.2.1]-hept-2-yl]-5-heptenoic acid, methyl ester for [1α,2β(5Z),3β,4α,5α,6α]-7-[5,6-epoxy-3-(hydroxymethyl)-7-oxabicyclo[2.2.1]hept-2-yl]-5-heptenoic acid, the title compound is obtained.

EXAMPLE 24

[1α,2β(5Z),3β,4α,5α,6α]-7-[5,6-Epoxy-3-[4-7-oxabicyclo[2.2.1]hept-2yl]-5-heptenoic acid Following the procedure of Example 21 except substituting benzyl methanesulfonate for n-hexyl methanesulfonate, the title compound is obtained.

EXAMPLE 25

Tris(hydroxymethyl)aminomethane salt of [1α,2β(5Z),-3β,4α,5α,6α]-7-[5,6-Epoxy-3-[(hexyloxy)methyl]-7-oxabicyclo[2.2.1]hept-2-yl]-5-heptenoic acid A solution of the compound formed in Example 3 in methanol is treated with an equivalent of tri(hydroxymethyl)aminomethane. The solvent is removed by evaporation to yield the title compound.

EXAMPLE 26

[1α,2β(5Z),3β,4α,5α,6α]-7-[5,6-Epoxy-3-[(methylthio)-methyl]-7-oxabicyclo[2.2.1]hept-2-yl]-5-heptenoic acid Following the procedure of Examples 1 and 2 except substituting methyl mercaptan from 1-hexanethiol, the title compound is obtained.

EXAMPLE 27

[1α,2β(5Z),3β,4α,5α,6α]-7-[5,6-Epoxy-3-[(Decylthio)-methyl]-7-oxabicyclo[2.2.1]hept-2-yl]-5-heptenoic acid Following the procedure of Examples 1 and 2 except substituting decylmercaptan for 1-hexanethiol, the title compound is obtained.

EXAMPLE 28

(1α,2β,3β,4α,5α,6α)-7-[5,6-Epoxy-3-[(butylthio)methyl]-7-oxabicyclo[2.2.1]hept-2-yl]heptanoic acid Following the procedure of Examples 1 and 6 except substituting butylmercaptan for 1-hexanethiol, the title compound is obtained.

EXAMPLE 29

[1α,2β(5Z),3β,4α,5α,6α]-7-[5,6-Epoxy-[(octylthio)-methyl]-7-oxabicyclo[2.2.1]hept-2-yl]-5-heptenoic acid Following the procedure of Examples 1 and 2 except substituting 1-octanethiol for 1-hexanethiol, the title compound is obtained.

EXAMPLE 30

[1α,2β(5Z),3β,4α,5α,6α]-7-[5,6-Epoxy-3-[(phenylthio)-methyl]-7-oxabicyclo[2.2.1]hept-2-yl]-5-heptenoic acid Following the procedure of Examples 1 and 2 except substituting phenylmercaptan for 1-hexanethiol, the title compound is obtained.

EXAMPLE 31 (1α,2β, 3β,4α,5α,6α)-7-[5,6-Epoxy-3-[(phenylthio)methyl]-7-oxabibicyclo[2.2.1]hept-2-yl]heptanoic acid Following the procedure of Examples 1, 2 and 6 except substituting phenylmercaptan for 1-hexanethiol, the title compound is obtained.

EXAMPLE 32

[1α,2β(5Z),3β,4α,5α,6α]-7-[5,6-Epoxy-3-[(ethylthio)-methyl]-7-oxabicyclo[2.2.1]hept-2-yl]-5-heptenoic acid
Following the procedure of Examples 1 and 2 except substituting ethylmercaptan for 1-hexanethiol, the title compound is obtained.

EXAMPLE 33

[1α,2β(5Z),3β,4α,5α,6α]-7-[5,6-Epoxy-3-[(benzylthio)-methyl]-7-oxabicyclo[2.2.1]hept-2-yl]-5-heptenoic acid Following the procedure of Examples 1 and 2 except subtituting benzylmercaptan for 1-hexanethiol, the title product is obtained.

EXAMPLE 34

[1α,2β(5Z),3β,4α,5α,6α]-7-[5,6-Epoxy-3-[(cyclohexylthio)methyl]-7-oxabicyclo[2.2.1]hept-2-yl]-5-heptenoic acid Following the procedure of Examples 1 and 2 except substituting cyclohexylmercaptan for 1-hexanethiol, the title compound is obtained.

EXAMPLE 35

(1α,2β,3β,4α,5α,6α)-7-[5,6-Epoxy-3-[(cyclohexylthio)-methyl]-7-oxabicyclo[2.2.1]hept-2-yl]heptanoic acid Following the procedure of Examples 1, 2 and 6 except substituting cyclohexylmercaptan for 1-hexanethiol, the title product is obtained.

EXAMPLE 36

[1α,2β(5Z),3β,4α,5α,6α]-7-[5,6-Epoxy-3-[2-(hexylthio)ethyl]-7-oxabicyclo[2.2.1]hept-2-yl]-5-heptenoic acid Following the procedure of Examples 17, 1 and 2 except substituting the Example 17 part C alcohol for the alcohol used in Example 1, the title compound is obtained.

EXAMPLE 37

(1α,2β,3β,4α,5α,6α)-7-[5,6-Epoxy-3-[2-(hexylthio)ethyl]-7-oxabicyclo[2.2.1]hept-2-yl]heptanoic acid Following the procedure of Examples 17, 6, 1 and 2 except substituting the Example 17 Part C alcohol for the alcohol used in Example 1 Part L, the title compound is obtained.

EXAMPLE 38

[1α,2β(5Z),3β,4α,5α,6α]-7-[5,6-Epoxy-3-[2-(phenylthio)ethyl]-7-oxabicyclo[2.2.1]hept-2-yl]-5-heptenoic acid Following the procedure of Examples 17, 1 and 2 except substituting the Example 17 Part C alcohol for the alcohol used in Example 1, Part L and substituting phenylmercaptan for 1-hexanethiol (of Example 1), the title compound is obtained.

EXAMPLE 39

(1α,2β,3β,4α,5α,6α)-7-[5,6-Epoxy-3-[2-(phenylthio)ethyl]-7-oxabicyclo[2.2.1]hept-2-yl]heptanoic acid Following the procedure of Examples 6, 17, 1 and 2 except substituting the Example 17, Part C alcohol for the alcohol used in Example 1, Part L and substituting phenylmercaptan for 1-hexanethiol (of Example 1), the title compound is obtained.

EXAMPLE 40

[1α,2β(5Z),3β,4α,5α,6α]-7-[5,6-Epoxy-3-[2-(benzylthio)ethyl]-7-oxabicyclo[2.2.1]hept-2-yl]-5-heptenoic acid Following the procedure of Examples 17 and 1 except substituting the Example 17 Part C alcohol for the alcohol used in Example 1, Part L and substituting benzylmercaptan for 1-hexanethiol (of Example 1), the title compound is obtained.

EXAMPLE 41

[1α,2β(5Z),3β,4α,5α,6α]-7-[5,6-Epoxy-3-[2-(cyclopentylthio)ethyl]-7-oxabicyclo[2.2.1]hept-2-yl]-5-heptenoic acid Following the procedure of Examples 17, 1 and 2 except substituting the Example 17B alcohol for the alcohol used in Example 1, Part L and substituting cyclopentylmercaptan for 1-hexanethiol (of Example 1), the title compound is obtained.

EXAMPLE 42

[1α,2β(5Z),3β,4α,5α,6α]-7-[5,6-Epoxy-3-[2-(Cyclohexylthio)ethyl]-7-oxabicyclo[2.2.1]hept-2-yl]-5-heptenoic acid Following the procedure of Examples 17 and 1 except substituting the Example 17C alcohol for the alcohol used in Example 1, Part L and substituting cyclohexylmercaptan for 1-hexanethiol (of Example 1), the title product is obtained.

EXAMPLE 43

[1α,2β(5Z),3β,4α,5α,6α]-7-[5,6-Epoxy-3-[4-(hexylthio)butyl]-7-oxabicyclo[2.2.1]hept-2-yl]-5-heptenoic acid Following the procedure of Examples 21, 1 and 2 except substituting the Example 21 Part C alcohol for the alcohol used in Example A, the title compound is obtained.

EXAMPLE 44

[1α,2β(5Z),3β,4α,5α,6α]-7-[5,6-Epoxy-3-[4-(cyclohexylthio)butyl]-7-oxabicyclo[2.2.1]hept-2-yl]-5-heptenoic acid Following the procedure of Example 43 except substituting cyclohexylmercaptan for 1-hexanethiol, the title compound is obtained.

EXAMPLE 45

[1α,2β(5Z),3β,4α,5α,6α]-7-[5,6-Epoxy-3-[4-(phenylthio)butyl]-7-oxabicyclo[2.2.1]hept-2-yl]-5-heptenoic acid Following the procedure of Example 43 except substituting phenylmercaptan for 1-hexanethiol, the title compound is obtained.

EXAMPLE 46

[1α,2β(5Z),3β,4α,5α,6α]-7-[5,6-Epoxy-3-[4-(benzylthio)butyl]-7-oxabicyclo[2.2.1]hept-2-yl]-5-heptenoic acid Following the procedure of Example 43 except substituting benzylmercaptan for 1-hexanethiol, the title compound is obtained.

EXAMPLE 47 AND 47A

[1α,2β(5Z),3β,4α,5α,6α]-7-[5,6-Epoxy-3-[(hexylsulfinyl)methyl]-7-oxabicyclo[2.2.1]hept-2-yl]5-heptenoic acid, methyl ester (Example 47) and

[1α,2β(5Z),3β,4α,5α,6α]-7-[5,6-Epoxy-3-[(hexylsulfonyl)methyl]-7-oxabicyclo[2.2.1]hept-2-yl]-5-heptenoic acid, methyl ester (Example 47A)

To a solution of 657 mg (1.72 mmol) of [1α,2β(5Z),3β,4α,5α,6α]-7-[5,6-epoxy-3-[(hexylthio)-methyl]-7-oxabicyclo[2.2.1]hept-2-yl]-5-heptenoic acid, methyl ester (prepared as described in Example 1) in 6.78 ml of methanol at 0° C is added dropwise over 4 minutes 8.37 ml of 0.5M aqueous sodium periodate solution. Tetrahydrofuran (2 ml) is then added and the resulting reaction mixture is stirred at room temperature for 15 hours. A precipitate is removed by filtration and washed with ether (3×50 ml). The filtrate is washed with 60 ml of saturated aqueous NaHCO₃ solution and dried over anhydrous magnesium sulfate. Concentration in vacuo affords an oily crude product. This is chromatographed on silica gel 60 using 0.5–1.0% CH₃OH in CH₂Cl₂ as eluant to give the title products.

EXAMPLE 48

[1α,2β(5Z),3β,4α,5α,6α]-7-[5,6-Epoxy-3-[(hexylsulfinyl)methyl]-7-oxabicyclo[2.2.1]hept-2-yl]-5-heptenoic acid To a stirred solution of 163 mg (0.41 mmol) of [1α,2β(5Z),3β,4α,5α,6α]-7-[5,6-epoxy-3-[(hexylsulfinyl)methyl]-7-oxabicyclo[2.2.1]hept-2-yl]- 5-heptenoic acid, methyl ester (Example 47) in 20.3 ml of THF and 3.09 ml of H₂O under argon is added 3.90 ml of 1N aqueous lithium hydroxide solution. This mixture is purged with argon vigorously for 10 minutes and stirred at room temperature for 6 hours. The reaction mixture is acidified to pH 4 by addition of 1N aqueous NaCl solution. The resulting solution is saturated with solid NaCl and extracted with EtOAc (4×50 ml). The combined EtOAC extracts are dried (MgSO₄), filtered and concentrated in vacuo to give 165 mg of crude acid. Purification is effected by flash chromatography on 20 g of silica gel 60 using 3% CH₃OH in CH₂Cl₂ as eluant. This affords title acid which solidifies on storage in the freezer.

EXAMPLE 48A

[1α,2β(5Z),3β,4α,5α,6α]-7-[5,6-Epoxy-3-[(Hexyl-sulfonyl)methyl]-7-oxabicyclo[2.2.1]hept-2-yl]-5-heptenoic acid To a stirred solution of 228 mg (0.55 mmol) of [1α,2β(5Z),3β,4α,5α,6α]-7-[5,6-epoxy-3-[(hexylsulfonyl)methyl]-7-oxabicyclo[2.2.1]hept-2-yl]-5-heptenoic acid, methyl ester (fast moving isomer) prepared in Example 47A in 27.0 ml of THF and 4.11 ml of H₂O under argon is added 5.19 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 50 ml of saturated NaCl solution. The resulting solution is saturated with solid NaCl and extracted with EtOAc (4×100 ml). The combined EtOAc extracts are dried (MgSO₄), filtered and concentrated in vacuo to give crude acid. Purification is effected by flash chromatography on 20.2 g of silica gel 60 using 3% CH₃OH in CH₂Cl₂ as eluant to give the title acid as a white solid.

EXAMPLE 49

[1α,2β(5Z),3β,4α,5α,6α]-7-[5,6-Epoxy-3-[(methylsulfinyl)methyl]-7-oxabicyclo2.2.1]hept-2-yl]-5-heptenoic acid Following the procedure of Exaples 1, 2, 47 and 48 except substituting methyl mercaptan for 1-hexanethiol, the title compound is obtained.

EXAMPLE 50

[1α,2β(5Z),3β,4α,5α,6α]-7-[5,6-Epoxy-3-[(ethylsulfinyl)methyl]-7-oxabicyclo[2.2.1]hept-2-yl]-5-heptenoic acid Following the procedure of Examples 1, 2, 47 and 48 except substituting ethylmercaptan for 1-hexanethiol, the title compound is obtained.

EXAMPLE 51

(1α,2β,3β,4α,5α,6α)-7-[5,6-Epoxy-3-[(heptylsulfinyl)-methyl]-7-oxabicyclo[2.2 1]hept-2-yl]-5-heptenoic acid Following the procedure of Examples 1, 6, 47 and 48 except substituting 1-heptanethiol for 1-hexanethiol, the title compound is obtained.

EXAMPLE 52

[1α,2β(5Z),3β,4α,5α,6α]-7-[5,6-Epoxy-3-[(benzylsulfinyl)methyl]-7-oxabicyclo[2.2.1]hept-2-yl]-5-heptenoic acid Following the procedure of Examples 1, 2, 47 and 48 except substitutin9 benzylmercaptan for 1-hexanethiol, the title compound is obtained.

EXAMPLE 53

[1α,2β(5Z),3β,4α,5α,6α]-7-[5,6-Epoxy-3-(cyclohexylmethylsulfinyl)methyl]-7-oxabicyclo[2.2.1]hept-2-yl]-5-heptenoic acid Following the procedure of Examples 1, 2, 47 and 48 except substituting cyclohexylmethyl mercaptan for 1-hexanethiol, the title compound is obtained.

EXAMPLE 54

[1α,2β(5Z),3β,4α,5α,6α]-7-[5,6-Epoxy-3-[(cyclopentylethylsulfinyl)methyl]-7-oxabicyclo[2.2.1]hept-2-yl]-5-heptenoic acid Following the procedure of Examples 1, 2, 47 and 48 except substituting cyclopentylethyl mercaptan for 1-hexanethiol, the title compound is obtained.

EXAMPLE 55

[1α,2β(5Z),3β,4α,5α,6α]-7-[5,6-Epoxy-3-[(octylsulfonyl)methyl]-7-oxabicyclo[2.2.1]hept-2-yl]-5-heptenoic acid Following the procedure of Examples 1, 2, 47A and 48A except substituting octylmercaptan for 1-hexanethiol, the title compound is obtained.

EXAMPLE 56

[1α,2β(5Z),3β,4α,5α,6α]-7-[5,6-Epoxy-3-[(propylsulfonyl)methyl]-7-oxabicyclo[2.2.1]-hept-2-yl]-5-heptenoic acid Following the procedure of Examples 1, 2, 47A and 48A except substituting propylmercaptan for 1-hexanethiol, the title compound is obtained.

EXAMPLE 57

[1α,2β(5Z),3β,4α,5α,6α]-7-[5,6-Epoxy-3-[(phenylsulfonyl)methyl]-7-oxabicyclo[2.2.1]hept-2-yl]-5-heptenoic acid Following the procedure of Examples 1, 2, 47A and 48A except substituting phenylmercaptan for 1-hexanethiol, the title compound is obtained.

EXAMPLE 58

[1α,2β(5Z),3β,4α,5α,6α]-7-[5,6-Epoxy-3-[(benzylsulfonyl)methyl]-7-oxabicyclo[2.2.1]hept-2-yl]-5-heptenoic acid Following the procedure of Examples 1, 2, 47A and 48A except substituting benzylmercaptan for 1-hexanethiol, the title compound is obtained.

EXAMPLE 59

[1α,2β(5Z),3β,4α,5α,6α]-7-[5,6-Epoxy-3-[(cyclohexylsulfonyl)methyl]-7-oxabicyclo[2.2.1]hept-2-yl]-5-heptenoic acid Following the procedure of Examples 1, 2, 47A and 48A except substituting cyclohexylmercaptan for 1-hexanethiol, the title compound is obtained.

EXAMPLE 60

[1α,2β(5Z),3β,4α,5α,6α]-7-[5,6-Epoxy-3-[(2-pentylsulfinyl)ethyl]-7-oxabicyclo[2.2.1]hept-2-yl]-5-heptenoic acid Following the procedure of Examples 3, 1, 2, 47 and 48 except substituting 1-pentanethiol for 1-hexanethiol, the title compound is obtained.

EXAMPLE 61

[1α,2β(5Z),3β,4α,5α,6α]-7-[5,6-Epoxy-3-[2-(phenylsulfonyl)ethyl]-7-oxabicyclo[2.2.1]hept-2-yl]-5-heptenoic acid Following the procedure of Examples 36, 1, 2, 47A and 48A except substituting phenylmercaptan for 1-hexanethiol, the title compound is obtained.

EXAMPLE 62

[1α,2β(5Z),3β,4α,5α,6α]-7-[5,6-Epoxy-3-[2-(cyclohexylsulfonyl)ethyl]-7-oxabicyclo[2.2.1]hept-2-yl]-5-heptenoic acid Following the procedure of Examples 36, 1, 2, 47A and 48A except substituting cyclohexylmercaptan for 1-hexanethiol, the title compound is obtained.

EXAMPLE 63

[1α,2β(5Z),3β,4α,5α,6α]-7-[5,6-Epoxy-3-[2-(benzylsulfinyl)ethyl]-7-oxabicyclo[2.2.1]hept-2-yl]-5-heptenoic acid Following the procedure of Examples 36, 1, 2, 47 and 48 except substituting benzylmercaptan for 1-hexanethiol, the title compound is obtained.

EXAMPLE 64

1α,2β(Z),3β(E),4α,5α,6α]-[5,6-Epoxy-3-[[(4-phenyl-2-butenyl)thio]methyl]-7-oxabicyclo[2.2.1]hept-2-yl-5-heptenoic acid Following the procedure of Examples 1 and 2 except substituting 4-phenyl-2-butenylthiol for 1-hexanethiol, the title compound is obtained.

EXAMPLE 65

[1α,2β(Z),3β(E),4α,5α,6α]-[5,6-Epoxy-3-[[(3-cyclohexyl-2-propenyl)oxy]methyl]-7-oxabicyclo[2.2.1]hept-2-yl]-5-heptenoic acid Following the procedure of Example 3 except substituting (E)-3-cyclohexyl-2-propenylmesylate for 1-hexane mesylate, the title compound is obtained.

EXAMPLE 66

(1α,2β,3β,4α,5α,6α)-7-[5,6-Epoxy-3-[[(4-cyclohexyl-2-butenyl)thio]methyl]-7-oxabicyclo[2.2.1]hept-2-yl]heptanoic acid Following the procedure of Examples 1, 2 and 6 except substituting 4-cyclohexyl-2-butenylthiol for 1-hexanethiol, the title compound is obtained.

EXAMPLE 67

[1α,2β(5Z),3β,4α,5α,6α]-7-[5,6-Epoxy-3-[[(2,3-dimethyl-2-heptenyl)oxy]methyl]-7-oxabicyclo[2.2.1]hept-2-yl]-5-heptenoic acid Following the procedure of Example 3 except substituting 2,3-dimethyl-2-heptenylmesylate for 1-hexane mesylate, the title compound is obtained.

EXAMPLE 68

[1α,2β(5Z),3β,4α,5α,6α]-7-[5,6-Epoxy-3-[[(3-ethyl-3-octenyl)thio]methyl]-7-oxabicyclo[2.2.1]hept-2-yl]-5-heptenoic acid Following the procedure of Examples 1 and 2 except substituting 3-ethyl-3-octenylthiol for 1-hexanethiol, the title compound is obtained.

EXAMPLE 69

(1α,2β,3β,4α,5α,6α)-7-[5,6-Epoxy-3-[(5-phenyl-4-pentenyl)oxy]methyl]-7-oxabicyclo[2.2.1]hept-2-yl]heptanoic acid Following the procedure of Examples 6 and 3 except substituting 5-phenyl-4-pentenylmesylate for 1-hexanemesylate, the title compound is obtained.

EXAMPLE 70

[1α,2β(5Z),3β,4α,5α,6α]-7-[5,6-Epoxy-3-[[(8-phenyl-5-octynyl)thio]methyl]-7-oxabicyclo[2.2.1]hept-2-yl]-5-heptenoic acid Following the procedure of Examples 1 and 2 except substituting 8-phenyl-5-octynylthiol for 1-hexanethiol, the title compound is obtained.

EXAMPLE 71

[1α,2β(5Z),3β,4α,5α,6α]-7-[5,6-Epoxy-3-[[(9-cyclohexyl-3-nonynyl)oxy]methyl]-7-oxabicyclo[2.2.1]hept-2-yl]-5-heptenoic acid Following the procedure of Example 3 except substituting 9-cyclohexyl-3-nonynylmesylate for 1-hexanemesylate, the title compound is obtained.

EXAMPLE 72

(1α,2β,3β,4α,5α,6α)-7-[5,6-Epoxy-3-[[(6-heptynyl)thio]methyl]-7-oxabicyclo[2.2.1]hept-2-yl]heptanoic acid Following the procedure of Exapmles 1 and 2 except substituting 5-heptynylthiol for 1-hexanethiol, the title compound is obtained.

EXAMPLE 73

[1α,2β(5Z),3β,4α,5α,6α]-7-[5,6-Epoxy-3-[[2-(3-phenyl-2-propenyl)thio]ethyl]-7-oxabicyclo[2.2.1]hept-2-yl]-5-heptenoic acid Following the procedure of Examples 17, 1 and 2 except substituting the Example 17 Part C alcohol for the alcohol used in Example 1 Part L and substituting 3-phenyl-2-propenylthiol for 1-hexanethiol, the title compound is obtained.

EXAMPLE 74

(1α,2β,3β,4α,5α,6α)-7-[5,6-Epoxy-3-[[2-(3-phenyl-2-propenyl)thio]ethyl]-7-oxabicyclo[2.2.1]hept-2-yl]heptanoic acid Following the procedure of Examples 1 and 6 except substituting the Example 73 compound for the Example 3 compound, the title compound is obtained.

EXAMPLE 75

[1α,2β(5Z),3β,4α,5α,6α]-7-[5,6-Epoxy-3-[[2-(6-phenyl-3-hexynyl)oxy]ethyl]-7-oxabicyclo[2.2.1]hept-2-yl]-5-heptenoic acid Following the procedure of Examples 17, 1 and 2 except substituting 6-phenyl-3-hexynylmesylate for 1-hexanemesylate, the title compound is obtained.

EXAMPLE 76

(1α,2β,3β,4α,5α,6α)-7-[5,6-Epoxy-3-[[2-(2-ethyl-3-methyl-2-heptenyl)thio]ethyl]-7-oxabicyclo[2.2.1]hept-2-yl]heptanoic acid Following the procedure of Examples 1, 6 and 17 except substituting 2-ethyl-3-methyl-2-heptenylthiol for 1-hexanethiol, the title compound is obtained.

EXAMPLE 77

[1α,2β(5Z),3β,4α,5α,6α]-7-[5,6-Epoxy-3-[[2-(3-cycloheptyl-2-propenyl)thio]ethyl]-7-oxabicyclo[2.2.1]hept-2-yl]-5-heptenoic acid Following the procedure of Examples 1, 6 and 17 except substituting 3-cycloheptyl-2-propenylthiol for 1-hexanethiol, the title compound is obtained.

EXAMPLE 78

[1α,2β(5Z),3β,4α,5α,6α]-7-[5,6-Epoxy-3-[[4-(3-phenyl-2-propenyl)thio]butyl]-7-oxabicyclo[2.2.1]hept-2-yl]-5-heptenoic acid Following the procedure of Examples 21, 1 and 2 except substituting the Example 21 Part C alcohol for the alcohol used in Example 1 and substituting 3-phenyl-2-propenylthiol for 1-hexanethiol, the title compound is obtained.

EXAMPLE 79

[1α,2β(5Z),3β,4α,5α,6α]-7-[5,6-Epoxy-3-[[4-(6-phenyl-3-hexynyl)oxy]butyl]-7-oxabicyclo[2.2.1]hept-2-yl]-5-heptenoic acid Following the procedure of Examples 21 and 3 except substituting 6-phenyl-3-hexynylmesylate for 1-hexanemesylate, the title compound is obtained.

EXAMPLE 80

[1α,2β(5Z),3β,4α,5α,6α]-7-[5,6-Epoxy-3-[[4-(7-phenyl-3-heptenyl)thio]butyl]-7-oxabicyclo[2.2.1]hept-2-yl]-5-heptenoic acid Following the procedure of Examples 78, 1 and 2 except substituting 7-phenyl-3-heptenylthiol for 3-phenyl-2-propenylthiol, the title compound is obtained.

EXAMPLE 81

(1α,2β,3β,4α,5α,6α)-7-[5,6-Epoxy-3-[[4-(6-hexenyl)thio]butyl]-7-oxabicyclo[2.2.1]hept-2-yl]heptanoic acid Following the procedure of Examples 1, 2, 6 and 78 except substituting 6-hexenylthiol for 3-phenyl-2-propenylthiol, the title compound is obtained.

EXAMPLE 82

[1α,2β(5Z),3β,4α,5α,6α]-7-[5,6-Epoxy-3-[[4-(7-heptynyl)thio]butyl]-7-oxabicyclo[2.2.1]hept-2-yl]-5-heptenoic acid Following the procedure of Examples 1, 2 and 78 except substituting 7-heptynylthiol for 3-phenyl-2-propenylthiol, the title compound is obtained.

EXAMPLE 83

[1α,2β(5Z),3β,4α,5α,6α]-7-[5,6-Epoxy-3-[(propyloxy)methyl]-7-oxabicyclo[2.2.1]hept-2-yl]-5-heptenoic acid Following the procedure of Example 3 except substituting propyl mesylate for hexyl mesylate, the title compound is obtained.

It will also be appreciated that the carboxybutyl triphenylphosphonium bromide of the structure

Br (C₆H₅)₃P(CH₂)₃—COOH employed in forming the upper side chain in the aforementioned examples may be replaced by

Br(C₆H₅)₃P(CH₂)ₙ₊₁COOH wherein (CH₂)ₙ is defined hereinbefore, to form compounds of the invention wherein the upper side chain is of the structure

—CH₂—A—(CH₂)ₙ₊—COOR wherein n is 0, 1, 2 or 4 to 8.

What is claimed is:

1. A compound of the structure

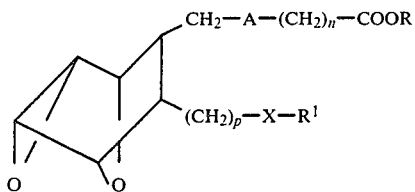

including all steroisomers thereof, wherein A is —CH=CH— or —CH₂—CH₂—; n is 0 to 8; p is 1 to 5; X is O or

wherein q is 0,1 or 2; R is H, lower alkyl, alkali metal or polyhydroxylamine salt; and R¹ is lower alkyl, aryl, arylalkyl, cycloalkyl, cycloalkylalkyl, lower alkenyl containing 2 to 12 carbons or lower alkynyl containing 2 to 12 carbons, wherein lower alkyl or alkyl alone or as part of another group contains 1 to 12 carbons and is unsubstituted or is substituted with halo, CF₃, alkoxy, aryl, alkyl-aryl, haloaryl, cycloalkyl, alkylcycloalkyl, hydroxy, alkylamino or alkylthiol;

- aryl alone or as part of another group contains 6 to 10 carbons in the ring portion and in unsubstituted or is substituted with 1 or 2 lower alkyl groups, 1 or 2 halogens, 1 or 2 hydroxy groups, 1 or 2 lower alkoxy groups, 1 or 2 alkylamino groups or 1 or 2 alkylthio groups;
- cycloalkyl alone or as part of another group contains 3 to 12 carbons and is unsubstituted or is substituted with 1 or 2 halogens, 1 or 2 lower alkyl groups and/or 1 or 2 lower alkoxy groups, an aryl group, 1 or 2 hydroxyl groups, 1 or 2 alkylamino groups or 1 or 2 alkylthio groups; and
- and (CH₂)ₙ (CH₂)ₚ include a straight or branched chain radical having 1 to 8 carbons in the normal chain in the case of (CH₂)ₙ and having 1 to 5 carbons in the normal chain in the case of (CH₂)ₚ and may contain 1 or 2 lower alkyl substituents.

2. The compound as defined in claim 1 wherein X is O.

3. The compound as defined in claim 1 wherein X is S.

4. The compound as defined in claim 1 wherein p is 1.

5. The compound as defined in claim 1 wherein n is 3 to 5.

6. The compound as defined in claim 1 wherein A is CH=CH, p is 1, n is 3 to 5, R is H and R¹ is lower alkyl.

7. The compound as defined in claim 1 wherein R¹ is propyl, butyl, pentyl, hexyl or heptyl including all isomers thereof.

8. The compound as defined in claim 1 having the name [1α,2β(5Z),3β,4α,5α,6α]-7-[5,6-epoxy-3-[(hexylthio)methyl]-7-oxabicyclo[2.2.1]hept-2-yl]-5-heptenoic acid or the methyl ester or hexyl ester thereof including all stereoisomers thereof.

9. The compound as defined in claim 1 having the name [1α,2β(5Z),3β,4α,5α,6α)-7-[5,6-epoxy-3-[(hexyloxy)methyl]-7-oxabicyclo[2.2.1]hept-2-yl]-5-heptenoic acid on the methyl ester thereof including all stereoisomers thereof.

10. The compound as defined in claim 1 [1α,2β(Z),3β,4α,5α,6α]-7-5,6-epoxy-3-[(propylthio)methyl]-7-oxalucyclo[2.2.1]hept-2-yl]-5-heptenoic acid or the methyl ester thereof including all stereoisomers thereof.

11. A method of inhibiting arachidonic acid-induced platelet aggregation and broncho-constriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation, inhibiting bronchoconstriction or inhibiting or reducing inflammation, which comprises adminstering to a mammalian host an effective amount of a compound as defined in claim 1 or a pharmaceutically acceptable salt thereof.

15. A method for treating peripheral vascular disease, which comprises topically or systemically adminstering to a mammalian host an effective ammount of a compound as defined in claim 1 or a pharmeceutically acceptable salt thereof.

* * * * *

UNITED STATES PATENT AND TRADEMARK OFFICE
CERTIFICATE OF CORRECTION

PATENT NO. : 4,611,006
DATED : September 9, 1986
INVENTOR(S) : Jagabandhu Das

It is certified that error appears in the above-identified patent and that said Letters Patent is hereby corrected as shown below:

Column 4, line 56, "P is 1" should read --p is 1--.
Column 15, line 40, delete "heptene 5.88".
Column 15, line 41, before "mmole)" insert --To a solution of Part H epoxy-nitrile (1.57 g, 5.88--.
Column 22, line 10, before "5,6" insert --[--.
Column 22, line 31, "4-7" should read --4-(benzyloxy)butyl]-7 --.
Column 23, line 18, "oxabibicyclo" should read --oxabicyclo--.
Column 31, line 40, after "$(CH_2)_n$" and before "$(CH_2)_p$" insert --and--.
Column 32, line 21 should read --[1β,2α(Z),3α,4β,5α,6α]-7-[5,6-epoxy-3-[(propylthio)me- --.

Column 31, line 40, before "$(CH_2)_n$" delete "and".

Signed and Sealed this

Twenty-third Day of December, 1986

*Attest:*

DONALD J. QUIGG

*Attesting Officer*     *Commissioner of Patents and Trademarks*